(12) United States Patent
Gong et al.

(10) Patent No.: US 12,037,422 B2
(45) Date of Patent: Jul. 16, 2024

(54) GEL MATERIAL

(71) Applicants: NATIONAL UNIVERSITY CORPORATION HOKKAIDO UNIVERSITY, Sapporo (JP); TORAY INDUSTRIES, INC., Tokyo (JP)

(72) Inventors: Jian Ping Gong, Sapporo (JP); Takayuki Kurokawa, Sapporo (JP); Honglei Guo, Sapporo (JP); Takahiro Matsuda, Sapporo (JP); Chengtao Yo, Sapporo (JP)

(73) Assignees: NATIONAL UNIVERSITY CORPORATION HOKKAIDO UNIVERSITY, Hokkaido (JP); TORAY INDUSTRIES, INC., Tokyo (JP)

( * ) Notice: Subject to any disclaimer, the term of this patent is extended or adjusted under 35 U.S.C. 154(b) by 497 days.

(21) Appl. No.: 17/270,973

(22) PCT Filed: Aug. 27, 2019

(86) PCT No.: PCT/JP2019/033428
§ 371 (c)(1),
(2) Date: Feb. 24, 2021

(87) PCT Pub. No.: WO2020/045387
PCT Pub. Date: Mar. 5, 2020

(65) Prior Publication Data
US 2021/0253753 A1    Aug. 19, 2021

(30) Foreign Application Priority Data
Aug. 28, 2018  (JP) .................................. 2018-159783

(51) Int. Cl.
*C08F 112/14* (2006.01)
*A61L 27/16* (2006.01)
(Continued)

(52) U.S. Cl.
CPC .......... *C08F 112/30* (2020.02); *C08F 112/26* (2020.02); *C08J 3/075* (2013.01);
(Continued)

(58) Field of Classification Search
CPC ...................................................... G02B 1/041
See application file for complete search history.

(56) References Cited

U.S. PATENT DOCUMENTS

| 2006/0015083 A1 | 1/2006 | Munro et al. |
| 2006/0068014 A1 | 3/2006 | Munro et al. |
| 2017/0258571 A1 | 9/2017 | Gong et al. |

FOREIGN PATENT DOCUMENTS

| JP | 48-7259 | 3/1973 |
| JP | 1-210605 A | 8/1989 |

(Continued)

OTHER PUBLICATIONS

International Search Report, issued in PCT/JP2019/033428, dated Nov. 26, 2019.
(Continued)

*Primary Examiner* — Michael F Pepitone
(74) *Attorney, Agent, or Firm* — Birch, Stewart, Kolasch & Birch, LLP (57) ABSTRACT

Disclosed is a gel material having a high water content and excellent mechanical properties. The gel material includes repeating units derived from the following monomers (A) and (B): (A) an anionic monomer containing a polymerizable carbon-carbon multiple bond and an aromatic ring, and (B) a cationic monomer containing a polymerizable carbon-carbon multiple bond and an aromatic ring. The gel material has a water content of 20% by mass to 95% by mass, a tensile elastic modulus of 9 MPa to 1000 MPa, and a tensile elongation at break of 50% to 5000%.

18 Claims, 6 Drawing Sheets

(51) Int. Cl.
 *A61L 27/52* (2006.01)
 *C08J 3/075* (2006.01)
 *G02B 1/04* (2006.01)

(52) U.S. Cl.
 CPC .............. *G02B 1/041* (2013.01); *A61L 27/16* (2013.01); *A61L 27/52* (2013.01); *A61L 2430/16* (2013.01)

(56) References Cited

FOREIGN PATENT DOCUMENTS

| JP | 2004-292648 A | 10/2004 |
| --- | --- | --- |
| JP | 2005-526879 A | 9/2005 |
| JP | 2006-503118 A | 1/2006 |
| JP | 2017-531737 A | 10/2017 |

OTHER PUBLICATIONS

Written Opinion of the International Searching Authority, issued in PCT/JP2019/033428, dated Nov. 26, 2019.
Extended European Search Report for European Application No. 19856378.5, dated Mar. 25, 2022.
Kudaibergenov, "Advances in Synthetic Polyampholytes for Biotechnology and Medicine," Review Journal of Chemistry, vol. 10, No. 1-2, 2020, pp. 12-39, 28 pages total.
Morisada et al., "Temperature-swing adsorption of aromatic compounds in water using polyampholyte gel," Adsorption, vol. 14, 2008, pp. 621-628, 8 pages total.
Sun et al., "Physical hydrogels composed of polyampholytes demonstrate high toughness and viscoelasticity," Nature Materials, vol. 12, 2013, pp. 932-937, 6 pages total.

GEL MATERIAL

CROSS-REFERENCE TO RELATED APPLICATIONS

This application is the National Stage Application under 35 U.S.C. § 371 of International Application No. PCT/JP2019/033428, filed on Aug. 27, 2019, which claims the benefit under 35 U.S.C. § 119(a) to Japanese Patent Application No. 2018-159783, filed on Aug. 28, 2018, all of which are hereby expressly incorporated by reference into the present application.

TECHNICAL FIELD

The present invention relates to a gel material.

BACKGROUND ART

Gel materials are materials having a three-dimensional network structure formed by cross-linking of polymers, which structure contains a liquid absorbed therein to form a swollen structure. A gel material containing water as the liquid is specifically called a hydrogel material.

Gel materials are useful materials drawing attention because of their excellent flexibility and liquid-holding properties. Their application to a variety of fields such as fields of medical care and pharmaceuticals, foods, civil engineering, bioengineering, and sports is expected.

Although polymers cross-linked through covalent bonds are common as gel materials, polymers cross-linked by a physical interaction such as ionic bonding, electrostatic interaction, or hydrophobic interaction are also known. Non-patent Documents 1 to 3 disclose gel materials cross-linked through ionic bonds (ionically bound gel materials). Non-patent Document 4 discloses a gel adsorbent cross-linked through covalent bonds.

PRIOR ART DOCUMENTS

Non-Patent Documents

[Non-patent Document 1] Nature Materials, 12, 932 (2013)
[Non-patent Document 2] Nature Materials, Supplementary Information, DOI: 10.1038/NMAT3713 (2013)
[Non-patent Document 3] Macromolecules, 50, 2923 (2017)
[Non-patent Document 4] Adsorption, 14, 621 (2008)

SUMMARY OF THE INVENTION

Problems to be Solved by the Invention

A challenge to be addressed for gel materials is improvement of their mechanical properties. Since a gel material holds a liquid therein, the liquid acts as a plasticizer, leading to insufficient mechanical properties, that is, leading to softness (low tensile elastic modulus), which is problematic.

For example, the ionically bound gel materials disclosed in Non-patent Documents 1 to 3 remain to be improved from the viewpoint of the fact that they have low tensile elastic moduli, that is, from the viewpoint of their softness.

An object of the present invention is to solve the above problem, to thereby provide a gel material having a high water content and excellent mechanical properties.

Means for Solving the Problems

For achievement of the object, the present invention provides the following.

(1) A gel material comprising repeating units derived from the following monomers (A) and (B):
  (A) an anionic monomer containing a polymerizable carbon-carbon multiple bond and an aromatic ring; and
  (B) a cationic monomer containing a polymerizable carbon-carbon multiple bond and an aromatic ring;
the gel material having
  a water content of 20% by mass to 95% by mass,
  a tensile elastic modulus of 9 MPa to 1000 MPa, and
  a tensile elongation at break of 50% to 5000%.

(2) The gel material according to (1), which is heat-moldable at a temperature within the range of 60° C. to 250° C.

(3) The gel material according to (1) or (2), comprising a copolymer containing repeating units derived from the monomers (A) and (B).

(4) The gel material according to any one of (1) to (3), wherein the (A) is an anionic monomer represented by the following Formula (1):

[wherein
$X^1$ represents a group selected from the group consisting of (meth)acryloyl and vinyl;
$Z^1$ represents a group selected from the group consisting of sulfo and carboxy, or a salt thereof;
$L^1$ and $L^2$ each independently represent a direct bond, or $C_1$-$C_{10}$ alkylene;
$Y^1$ represents a direct bond, or a group selected from the group consisting of O, S, and N—$R^2$;
$Y^2$ represents a direct bond, or a group selected from the group consisting of O, S, N—$R^3$, OCO, and N—$R^4$CO;
$R^1$ represents a group selected from the group consisting of $C_1$-$C_{10}$ alkyl, phenyl, halogeno, and hydroxy;
$R^2$ to $R^4$ each independently represent hydrogen, or a group selected from the group consisting of $C_1$-$C_{10}$ alkyl and phenyl; and
m represents an integer of 0 to 4.]

(5) The gel material according to (4), wherein
the $L^1$ and $L^2$ are each independently a direct bond or $C_1$-$C_5$ alkylene;
the $Y^1$ and $Y^2$ are direct bonds; and
the $R^1$ is $C_1$-$C_5$ alkyl.

(6) The gel material according to any one of (1) to (5), wherein the (B) is a cationic monomer represented by the following Formula (2):

[wherein
X³ represents a group selected from the group consisting of (meth)acryloyl and vinyl;
Z³ represents amino or a salt thereof;
L³ and L⁴ each independently represent a direct bond, or $C_1$-$C_{10}$ alkylene;
Y³ represents a direct bond, or a group selected from the group consisting of O, S, and N—R⁶;
Y⁴ represents a direct bond, or a group selected from the group consisting of O, S, N—R⁷, OCO, and N—R⁸CO;
R⁵ represents a group selected from the group consisting of $C_1$-$C_{10}$ alkyl, phenyl, halogeno, and hydroxy;
R⁶ to R⁸ each independently represent hydrogen, or a group selected from the group consisting of $C_1$-$C_{10}$ alkyl and phenyl; and
n represents an integer of 0 to 4.]

(7) The gel material according to (6),
wherein
the Z³ is a quaternary ammonium salt;
the L³ and L⁴ are each independently a direct bond or $C_1$-$C_5$ alkylene;
the Y³ and Y⁴ are direct bonds; and
the R⁵ is $C_1$-$C_5$ alkyl.

(8) The gel material according to any one of (1) to (3), wherein the (A) is an anionic monomer selected from the group consisting of benzyl (meth)acrylate-based anionic monomers, benzyl (meth)acrylamide-based anionic monomers, phenyl (meth)acrylate-based anionic monomers, phenyl (meth)acrylamide-based anionic monomers, and styrene-based anionic monomers.

(9) The gel material according to any one of (1) to (3), wherein the (B) is a cationic monomer selected from the group consisting of benzyl (meth)acrylate-based cationic monomers, benzyl (meth)acrylamide-based cationic monomers, phenyl (meth)acrylate-based cationic monomers, phenyl (meth)acrylamide-based cationic monomers, and styrene-based cationic monomers.

(10) The gel material according to any one of (1) to (9), wherein the (A) is styrenesulfonic acid or a salt thereof.

(11) The gel material according to any one of (1) to (10), wherein the (B) is dialkylaminoalkyl styrene or a salt thereof.

(12) The gel material according to (11), wherein the (B) is (vinylbenzyl)trimethylammonium chloride.

(13) The gel material according to any one of (1) to (12), which is optically transparent.

(14) A medical gel material comprising the gel material according to any one of (1) to (13).

(15) An ophthalmic gel material comprising the medical gel material according to (14).

(16) An ophthalmic lens gel material comprising the ophthalmic gel material according to (15).

(17) A medical device comprising the medical gel material according to (14).

(18) The medical device according to (17), which is an ophthalmic lens.

Effect of the Invention

The gel material of the present invention is characterized in that it has a high tensile elastic modulus and is hard while having a high water content.

MODE FOR CARRYING OUT THE INVENTION

Since the gel material of the present invention is hydrous, has appropriate hardness (elastic modulus), and is hardly broken because of its toughness, the gel material is applicable to medical devices such as materials for artificial organs including artificial cartilage, artificial skin, artificial muscle, artificial breast, artificial joint, artificial cornea, and artificial blood vessel, tubes and lines to be introduced into a living body for carrying out infusion, gas transportation, drainage, or the like, tubes which include a therapeutic tool or monitoring tool therein, and which are to be introduced into a living body, blood purification filters, covering materials for covering a living-body surface to protect or treat the living-body surface, and carriers which include a drug or the like, and which are to be introduced into a living body; devices for biotechnology, such as cell culture sheets, and scaffold materials for tissue regeneration; ophthalmic lenses such as spectacle lenses, corneoscleral lenses, contact lenses, intraocular lenses, and corneal implants; agricultural/gardening devices such as moisture-retaining sheets and moisture-retaining materials; filtering devices; antifouling materials such as anti-biofouling materials, anti-protein-fouling materials, and anti-lipid-fouling materials; beauty devices such as facial packs; gel bodies to be used for base materials of aromatics, or for toiletry products and the like; vibration insulators; electrolyte materials to be used for batteries, power generation devices, electrolytic devices, and the like; actuators; shock-absorbing structures; industrial protective films; energy-related materials such as piezoelectric elements; and printing materials.

Unless otherwise specified, each physical property value in the present description is a value for a sample in the water-containing state.

In the present description, the water-containing state means the equilibrium water-containing state of the sample. The water-containing state is obtained by immersing a sample in pure water at room temperature (24° C.) for not less than 24 hours. For measurement of physical property values in the water-containing state, a test piece is removed from pure water, and water on its surface is briefly removed with clean cloth as soon as possible thereafter. The measurement is then carried out as soon as possible. Unless otherwise specified, the measurement of physical property values is carried out at room temperature (24° C.).

In the present invention, the dry state means the state after vacuum drying of a water-containing sample at 40° C. for not less than 16 hours in a vacuum dryer. Measurement of physical property values in the dry state is carried out as soon as possible after removing the test piece from the dryer as quickly as possible. Unless otherwise specified, the measurement of physical property values is carried out at room temperature (24° C.).

The water content in the present invention means a value obtained by measuring the mass (M1) of a sample in the water-containing state and the mass (M2) of the sample in the dry state, and performing calculation according to the following equation.

Water content (%)=(M1−M2)/M1×100

In the present description, "living body" mainly means a living body of a vertebrate including humans.

The gel material used in the present invention has a water content within the range of 20% by mass to 95% by mass. In cases where the water content is not less than 20% by mass, the gel material has good affinity to a living body, which is preferred. In cases where the water content is too low, the gel material has insufficient surface wettability, and/or adheres to a mucosal surface of a living body, which is not preferred. In cases where the water content is too high, the gel material exhibits a high level of shape change upon drying, which is not preferred. The lower limit of the water content is preferably 25% by mass, more preferably 30% by mass, still more preferably 35% by mass, still more preferably 40% by mass. The upper limit of the water content is preferably 90% by mass, more preferably 80% by mass, still more preferably 70% by mass, still more preferably 65% by mass. Any combination of the upper limit and lower limit may be employed.

The gel material of the present invention has a tensile elastic modulus of 9 MPa to 1000 MPa. In cases where the tensile elastic modulus is not less than 9 MPa, the material is sufficiently hard in view of application to a living body, so that the material is suitable as a structural material for various devices. In cases where the tensile elastic modulus is not more than 1000 MPa, the material is not too hard, so that the material does not cause discomfort or injury to a living body. Thus, the material is suitable as a structural material for various devices. The lower limit of the tensile elastic modulus is preferably 10 MPa, more preferably 20 MPa, still more preferably 30 MPa, still more preferably 50 MPa. The upper limit of the tensile elastic modulus is preferably 500 MPa, more preferably 300 MPa, still more preferably 200 MPa, still more preferably 100 MPa. Any combination of the upper limit and lower limit may be employed. Unless otherwise specified, the tensile elastic modulus in the present description is the tensile elastic modulus in the water-containing state.

The gel material of the present invention has a tensile elongation at break of 50% to 5000%. In cases where the tensile elongation at break is not more than 50%, the gel material is easily broken, which is not preferred. In cases where the tensile elongation at break is not less than 5000%, deformation of the gel material tends to occur, which is not preferred. The lower limit of the tensile elongation at break is preferably 80%, more preferably 100%, still more preferably 200%, still more preferably 300%. The upper limit of the tensile elongation at break is preferably 3000%, more preferably 2000%, still more preferably 1000%, still more preferably 800%. Any combination of the upper limit and lower limit may be employed. Unless otherwise specified, the tensile elongation at break in the present description is the tensile elongation at break in the water-containing state.

In one aspect, the gel material of the present invention is preferably heat-moldable. Once a gel material is formed, its remolding into another shape is generally difficult since the gel material has a three-dimensional network structure. However, a gel material formed by physical cross-linking can be heat-molded in some cases since dissociation of physical interaction occurs at a lower temperature compared to covalent bonding. In the gel material of the present invention, a three-dimensional network structure is formed by cross-linking through ionic bonds, which are physical interaction. Preferably, the amount of cross-links through covalent bonds in the gel material of the present invention is small enough not to prevent achievement of the heat moldability, or the gel material contains no such cross-links at all. The gel material more preferably does not contain such cross-links at all.

The gel material of the present invention is preferably heat-moldable at a temperature within the range of 60° C. to 250° C. The term "heat-moldable" herein means that, when a gel material is placed in water at a predetermined temperature, deformed into another shape, and then placed again into water at room temperature to allow recovery of the gel material into the water-containing state, the gel material is capable of retaining a desired shape (which is different from the original shape) even without continuous application of external stress. It should be noted that the gel material after heat molding needs to satisfy the physical property requirement defined by the present invention. Thus, for example, in cases where a liquid in the gel material is irreversibly lost in the process of heat molding, and hence the water content defined in the present invention is not achieved after the heat molding, the gel material is not regarded as heat-moldable. Further, for example, in cases where the gel material is once molded into another shape, but recovery of the gel material into the water-containing state causes the gel material to have the original shape again, the gel material is not regarded as heat-moldable. The heat molding temperature is preferably a temperature within the range of 60° C. to 200° C., more preferably a temperature within the range of 65° C. to 150° C., still more preferably a temperature within the range of 65° C. to 100° C., still more preferably a temperature within the range of 70° C. to 95° C. Any combination of the upper limit and lower limit of the temperature range may be employed. In cases where the heat molding temperature is higher than 100° C., the heat molding may be carried out in a pressure container.

In order for the gel material of the present invention to be heat-moldable, the gel material preferably has storage moduli within particular ranges at 40° C. and 70° C. in dynamic viscoelasticity measurement. The dynamic viscoelasticity measurement for the gel material of the present invention is carried out using a sample in the water-containing state. The storage modulus at 40° C. is preferably not less than 9 MPa, more preferably not less than 10 MPa. The storage modulus at 40° C. is preferably not more than 1000 MPa, more preferably not more than 100 MPa. Any combination of the upper limit and lower limit may be employed. The storage modulus of the gel material of the present invention at 70° C. is preferably not more than 0.1 MPa, more preferably not more than 0.08 MPa, still more preferably not more than 0.06 MPa. The storage modulus at 70° C. is preferably not less than 0.001 MPa, more preferably not less than 0.003 MPa, still more preferably not less than 0.005 MPa. Any combination of the upper limit and lower limit may be employed.

The gel material of the present invention is preferably optically transparent. In cases where the gel material is optically transparent, conditions in the opposite side separated by the gel material can be seen by the naked eye, which is preferred. The optically transparent gel material can be suitably used for medical devices, more specifically, ophthalmic medical devices, especially ophthalmic lenses.

The visible light transmittance of the gel material of the present invention is preferably not less than 70%, more preferably not less than 75%, still more preferably not less than 80% throughout the wavelength region of 400 nm to 800 nm. The visible light transmittance is measured using a sheet having a thickness of 1.3 to 1.5 mm in the water-containing state.

The gel material of the present invention comprises repeating units derived from the following monomers (A) and (B):
(A) an anionic monomer containing a polymerizable carbon-carbon multiple bond and an aromatic ring; and
(B) a cationic monomer containing a polymerizable carbon-carbon multiple bond and an aromatic ring.

Each of the monomers (A) and (B) may be either one kind of monomer or a combination of two or more kinds of monomers.

The term "(meth)" as used in the present description represents methyl substitution which is optional. Thus, for example, the term "(meth)acrylate" represents either methacrylate or acrylate. This also applies to terms such as "(meth)acrylamide" and "(meth)acryloyl".

The term "(meth)acrylate" as used in the present description represents a (meth)acrylic acid ester.

The term "monomer" as used in the present description represents a compound containing one or more polymerizable carbon-carbon multiple bonds.

The term "monomer composition" as used in the present description means a mixture containing monomers, a polymerization initiator, a solvent, and the like, which mixture has not yet been subjected to polymerization.

The "repeating unit" in the present description is described below. The "repeating unit" in the present invention represents a unit of repeating structure in a polymer, which repeating structure corresponds to the structure of a monomer produced by modification of a polymerizable carbon-carbon multiple bond(s) in the course of polymerization reaction of the monomer.

The monomers (A) and (B) each contain a polymerizable carbon-carbon multiple bond. Specific examples of groups containing the polymerizable carbon-carbon multiple bond include ethynyl, propargyl, vinyl, allyl, styryl, (meth)acryloyl, cyanoacryloyl, itaconate, maleate, and fumarate. Among these, from the viewpoint of ease of polymerization, styryl and (meth)acryloyl are preferred.

The monomers (A) and (B) each contain an aromatic ring. Preferred specific examples of the aromatic ring include a benzene ring, a naphthalene ring, an anthracene ring, a phenanthrene ring, a triphenylene ring, a tetraphene ring, a pyrene ring, a perylene ring, a fluorene ring, a furan ring, a thiophene ring, a benzofuran ring, and a benzothiophene ring. Among these, from the viewpoint of availability of monomers, a benzene ring, a naphthalene ring, and a fluorene ring are preferred. A benzene ring is most preferred.

The monomer (A) is an anionic monomer, and contains an anionic group. Specific examples of the anionic group include sulfonate, sulfate, carboxy, phosphonate, and phosphate. Among these, from the viewpoint of the anionic strength, sulfonate, sulfate, and carboxy are preferred. Sulfonate is especially preferred. These anionic groups may also be their corresponding salts. The salts are preferably metal salts, more preferably alkali metal salts.

The anionic monomer of (A) is preferably a compound represented by the following Formula (1):

[wherein
$X^1$ represents a group selected from the group consisting of (meth)acryloyl and vinyl;
$Z^1$ represents a group selected from the group consisting of sulfo and carboxy, or a salt thereof;
$L^1$ and $L^2$ each independently represent a direct bond, or $C_1$-$C_{10}$ alkylene;
$Y^1$ represents a direct bond, or a group selected from the group consisting of O, S, and N—$R^2$;
$Y^2$ represents a direct bond, or a group selected from the group consisting of O, S, N—$R^3$, OCO, and N—$R^4$CO;
$R^1$ represents a group selected from the group consisting of $C_1$-$C_{10}$ alkyl, phenyl, halogeno, and hydroxy;
$R^2$ to $R^4$ each independently represent hydrogen, or a group selected from the group consisting of $C_1$-$C_{10}$ alkyl and phenyl; and
m represents an integer of 0 to 4.]

$X^1$ is preferably vinyl.
$Z^1$ is preferably sulfo or a salt thereof.
$L^1$ is preferably a direct bond or $C_1$-$C_5$ alkylene, more preferably a direct bond or $C_1$-$C_2$ alkylene, still more preferably a direct bond.
$L^2$ is preferably a direct bond or $C_1$-$C_5$ alkylene, more preferably a direct bond or methylene, still more preferably a direct bond.
$Y^1$ is preferably a direct bond or a group selected from the group consisting of O and N—$R^2$, more preferably a direct bond or O, still more preferably a direct bond.
$Y^2$ is preferably a direct bond or OCO, more preferably a direct bond.

$R^1$ is preferably $C_1$-$C_5$ alkyl, more preferably a group selected from the group consisting of methyl, ethyl, and propyl, still more preferably methyl.

$R^2$ to $R^4$ are preferably each independently hydrogen or $C_1$-$C_5$ alkyl, more preferably a group selected from the group consisting of hydrogen, methyl, ethyl, and propyl, still more preferably hydrogen.

m is preferably 0 or 1, more preferably 0.

Especially preferably, in the Formula (1), the $L^1$ and $L^2$ are each independently a direct bond or $C_1$-$C_5$ alkylene; the $Y^1$ and $Y^2$ are direct bonds; and the $R^1$ is $C_1$-$C_5$ alkyl.

Preferred specific examples of the monomer (A) include styrenesulfonic acid, vinylbenzoic acid, vinyltoluenesulfonic acid, vinylnaphthalenesulfonic acid, carboxymethylstyrene, sulfomethylstyrene, vinylbenzylsulfuric acid, sulfomethylvinylnaphthalene, sulfoxymethylvinylnaphthalene, 2-methacryloyloxyethyl phthalate, and salts thereof. Styrenesulfonic acid and salts thereof are most preferred.

The monomer (B) is a cationic monomer, and contains a cationic group. Specific examples of the cationic group include amino and phosphine. From the viewpoint of cationic strength, amino is preferred. The amino may be substituted with one or two organic groups. In this case, each organic group is preferably $C_1$-$C_5$ alkyl. These cationic groups may also be their corresponding salts. In the case of a salt of amino, a quaternary ammonium salt is also preferred.

The cationic monomer of (B) is preferably a compound represented by the following Formula (2):

[wherein
$X^3$ represents a group selected from the group consisting of (meth)acryloyl and vinyl;
$Z^3$ represents amino or a salt thereof;
$Y^3$ represents a direct bond, or a group selected from the group consisting of O, S, and N—$R^6$;
$Y^4$ represents a direct bond, or a group selected from the group consisting of O, S, N—$R^7$, OCO, and N—$R^8$CO;
$R^5$ represents a group selected from the group consisting of $C_1$-$C_{10}$ alkyl, phenyl, halogeno, and hydroxy;
$R^6$ to $R^8$ each independently represent hydrogen, or a group selected from the group consisting of $C_1$-$C_{10}$ alkyl and phenyl; and
n represents an integer of 0 to 4.]

$X^3$ represents a group selected from the group consisting of (meth)acryloyl and vinyl, preferably vinyl.

$Z^3$ represents amino or a salt thereof. The amino may be substituted with one or two organic groups. In this case, each organic group is preferably $C_1$-$C_5$ alkyl, more preferably $C_1$-$C_3$ alkyl, still more preferably methyl. The amino may also be a corresponding salt. A quaternary ammonium salt is also preferred.

$L^3$ and $L^4$ each independently represent a direct bond or $C_1$-$C_{10}$ alkylene. $L^1$ is preferably a direct bond or $C_1$-$C_5$ alkylene, more preferably a direct bond or $C_1$-$C_2$ alkylene, still more preferably a direct bond. $L^2$ is preferably a direct bond or $C_1$-$C_5$ alkylene, more preferably a direct bond or methylene, still more preferably methylene.

$Y^3$ is preferably a direct bond or a group selected from the group consisting of O and N—$R^6$, more preferably a direct bond or O, still more preferably a direct bond.

$Y^4$ is preferably a direct bond or OCO, more preferably a direct bond.

$R^5$ is preferably $C_1$-$C_5$ alkyl, more preferably a group selected from the group consisting of methyl, ethyl, and propyl, still more preferably methyl.

$R^6$ to $R^8$ are preferably each independently hydrogen or $C_1$-$C_5$ alkyl, more preferably a group selected from the group consisting of hydrogen, methyl, ethyl, and propyl, still more preferably hydrogen.

n is preferably 0 or 1, more preferably 0.

Especially preferably, in the Formula (2), the $Z^3$ is a quaternary ammonium salt; the $L^3$ and $L^4$ are each independently a direct bond or $C_1$-$C_5$ alkylene; the $Y^3$ and $Y^4$ are direct bonds; and the $R^5$ is $C_1$-$C_5$ alkyl.

Preferred specific examples of the monomer (B) include aminostyrene, alkylaminostyrene, dialkylaminostyrene, aminoalkylstyrene, alkylaminoalkylstyrene, dialkylaminoalkylstyrene, and salts thereof. Here, each alkyl is preferably $C_1$-$C_5$ alkyl. In cases where a plurality of alkyl groups are present in each molecule, the alkyl groups may be different from each other. The alkyl is more preferably $C_1$-$C_3$ alkyl, most preferably methyl. Dialkylaminoalkylstyrene and salts thereof are preferred. More preferred specific examples thereof are vinylbenzyldimethylamine and vinylbenzyltrimethylammonium salt.

The ratio (mol/mol) between the repeating units derived from the monomer (A) and the repeating units derived from the monomer (B) is preferably within the range of 35/65 to 75/25, more preferably within the range of 40/60 to 65/35, still more preferably within the range of 45/55 to 60/40, still more preferably within the range of 49/51 to 57/43 from the viewpoint of easily obtaining a gel material having a high elastic modulus.

The gel material of the present invention may contain a repeating unit derived from a monomer [hereinafter referred to as (C)] other than the monomers (A) and (B). By the presence of the repeating unit(s) derived from the monomer (C), physical properties of the gel material can be controlled.

The monomer (C) contains a polymerizable carbon-carbon multiple bond. Specific examples of groups containing the polymerizable carbon-carbon multiple bond include ethynyl, propargyl, vinyl, allyl, styryl, (meth)acryloyl, cyanoacryloyl, itaconate, maleate, and fumarate. Among these, from the viewpoint of ease of polymerization, styryl and (meth)acryloyl are preferred.

Examples of the monomer (C) include (meth)acrylic acid, (meth)acrylates, (meth)acrylamides, N-vinylcarboxylic acid esters, N-vinylcarboxylic acid amides, N-vinyllactams, maleic acid, maleic acid esters, maleimides, itaconic acid, itaconic acid esters, and styrenes.

Examples of the monomer (C) include (meth)acrylic acid; (meth)acrylic acid alkyl esters whose alkyl group has 1 to 18 carbon atoms, such as methyl acrylate, methyl methacrylate, ethyl acrylate, ethyl methacrylate, n-butyl acrylate, n-butyl methacrylate, isobutyl acrylate, isobutyl methacrylate, tert-butyl acrylate, tert-butyl methacrylate, neopentyl acrylate, neopentyl methacrylate, octyl acrylate, octyl methacrylate, lauryl acrylate, lauryl methacrylate, lauryl acrylate, lauryl methacrylate, stearyl acrylate, stearyl methacrylate, cetyl acrylate, and cetyl methacrylate; cycloalxyl (meth)acrylates containing $C_6$-$C_{12}$ cycloalkyl, such as cyclohexyl acrylate and cyclohexyl methacrylate; (meth)acrylic acid aryl esters whose aralkyl group has 7 to 12 carbon atoms, such as benzyl acrylate and benzyl methacrylate; hydroxyalkyl (meth)acrylates whose hydroxyalkyl group has 2 to 6 carbon atoms, such as hydroxyethyl acrylate, hydroxyethyl methacrylate, hydroxypropyl acrylate, hydroxypropyl methacrylate, hydroxybutyl acrylate, and hydroxybutyl methacrylate; alkoxyalkyl (meth)acrylates whose alkoxyalkyl group has 2 to 8 carbon atoms, such as methoxyethyl acrylate, methoxyethyl methacrylate, methoxybutyl acrylate, and methoxybutyl methacrylate; alkylcarbitol (meth)acrylates whose alkyl group has 1 to 4 carbon atoms, such as ethylcarbitol acrylate and ethylcarbitol methacrylate; alkyl (meth)acrylamides whose alkyl group has 1 to 12 carbon atoms, such as N-methylacrylamide, N-methylmethacrylamide, N-ethylacrylamide, N-ethylmethacrylamide, N-propylacrylamide, N-propylmethacrylamide, N-isopropylacrylamide, N-isopropylmethacrylamide, N-tert-butylacrylamide, N-tert-butylmethacrylamide, N-octylacrylamide, N-octylmethacrylamide, N,N-dimethylacrylamide, N,N-dimethylmethacrylamide, N,N-diethylacrylamide, and N,N-diethylmethacrylamide; alkoxy (meth)acrylamides whose alkoxy group has 1 to 6 carbon atoms, such as N-butoxymethylacrylamide and N-butoxymethylmethacrylamide; (meth)acryloylmorpholines such as acryloylmorpholine and methacryloylmorpholine; diacetone (meth)acrylamides such as diacetone acrylamide and diacetone dimethacrylamide; styrene-based monomers such as styrene and methylstyrene; fatty acid alkyl esters whose alkyl group has 1 to 4 carbon atoms, other than (meth)acrylic acid alkyl esters, such as methyl itaconate and ethyl itaconate; fatty acid vinyl esters such as vinyl acetate and vinyl propionate; nitrogen-atom-containing monomers such as N-vinylpyrrolidone and N-vinylcaprolactam; sulfonic acids such as vinylsulfonic acid, allylsulfonic acid, acrylamidomethylpropanesulfonic acid, and methacrylamidomethylsulfonic acid; alkylene oxide-modified phosphoric acid (meth)acrylates such as ethylene oxide-modified phosphoric acid acrylate and ethylene oxide-modified phosphoric acid methacrylate; and betaine-based monomers such as N-acryloyloxyethyl-N,N-dimethylammonium-α-N-methylcarboxybetaine, N-methacryloyloxyethyl-N,N-dimethylammonium-α-N-methylcarboxybetaine, N-acryloyloxyethyl-N,N-diethylammonium-α-N-methylcarboxybetaine, N-methacryloyloxyethyl-N,N-diethylammonium-α-N-methylcarboxybetaine, N-acryloyloxyethyl-N,N-dimethylammonium-β-N-ethylcarboxybetaine, N-methacryloyloxyethyl-N,N-dimethylammonium-β-N-ethylcarboxybetaine, N-acryloyloxyethyl-N,N-diethylammonium-β-N-ethylcarboxybetaine, N-methaeryloyloxyethyl-N,N-diethylammonium-β-N-ethylcarboxybetaine, N-acrylamidopropyl-N,N-dimethylammonium-α-N-methylcarboxybetaine, N-methacrylamidopropyl-N,N-dimethylammonium-α-N-methylcarboxybetaine, N-acrylamidopropyl-N,N-diethylammonium-α-N-methylcarboxybetaine, N-methacrylamidopropyl-N, N-diethylammonium-α-N-methylcarboxybetaine, N-acrylamidopropyl-N,N-dimethylammonium-β-N-ethylcarboxybetaine, N-methacrylamidopropyl-N,N-dimethylammonium-β-N-ethylcarboxybetaine, N-acrylamidopropyl-N,N-diethylammonium-β-N-ethylcarboxybetaine, and N-methacrylamidopropyl-N,N-diethylammonium-β-N-ethylcarboxybetaine. These monomers may be used individually, or two or more of these may be used in combination.

The monomer (C) is preferably soluble in water or alcohol.

From the viewpoint of obtaining a gel material having excellent mechanical strength, the content of repeating units derived from the monomer (C) is preferably not more than 50% by mass, more preferably not more than 40% by mass, still more preferably not more than 30% by mass, still more preferably not more than 20% by mass with respect to the dry mass of the gel material. The lower limit is 0% by mass, but, from the viewpoint of controlling physical properties of the gel material, the content is preferably not less than 1% by mass, more preferably not less than 2% by mass, still more preferably not less than 3% by mass, still more preferably not less than 5% by mass. Any combination of the lower limit and upper limit may be employed.

The gel material of the present invention may contain a repeating unit derived from a multifunctional monomer (cross-linking monomer) having two or more polymerizable carbon-carbon multiple bonds.

Preferred examples of the cross-linking monomer include a (meth)acrylamide compound having two or more, preferably two, (meth)acryloyl groups; an aromatic compound having two or more, preferably two or three, polymerizable carbon-carbon double bonds; a (meth)acrylate compound having two or more, preferably two or three, (meth)acryloyl groups; a compound having two or more, preferably two or three, allyl groups; or the like. Among these, a (meth)acrylamide compound having two or more (meth)acryloyl groups may adversely affect mechanical properties, leading to, for example, fragility of the gel material. In view of this, an aromatic compound having two or more, preferably two or three, polymerizable carbon-carbon double bonds; or a (meth)acrylate compound having two or more, preferably two or three, (meth)acryloyl groups is preferred. A (meth)acrylate compound having two or more, preferably two or three, (meth)acryloyl groups is more preferred.

Preferred examples of the cross-linking monomer include (meth)acrylamide compounds having two or more, preferably two, (meth)acryloyl groups, such as alkylene bis(meth)acrylamide whose alkylene group has one to four carbon atoms, including methylene bisacrylamide and methylene bismethacrylamide; aromatic compounds having two or more, preferably two or three, polymerizable carbon-carbon double bonds, such as divinylbenzene and diallylbenzene; (meth)acrylate compounds having two or more, preferably two or three, (meth)acryloyl groups, such as ethylene diacrylate, ethylene dimethacrylate, ethylene glycol diacrylate, ethylene glycol dimethacrylate, propylene glycol diacrylate, propylene glycol dimethacrylate, diethylene glycol diacrylate, diethylene glycol dimethacrylate, triethylene glycol diacrylate, triethylene glycol dimethacrylate, 1,4-butanediol diacrylate, 1,4-butanediol dimethacrylate, 1,6-hexanediol diacrylate, 1,6-hexanediol dimethacrylate, 1,9-nonanediol diacrylate, 1,9-nonanediol dimethacrylate, 2-n-butyl-2-ethyl-1,3-propanediol diacrylate, 2-n-butyl-2-ethyl-1,3-propanediol dimethacrylate, tripropylene glycol diacrylate, tripropylene glycol dimethacrylate, tetraethylene glycol diacrylate, tetraethylene glycol dimethacrylate, trimethylolpropane triacrylate, trimethylolpropane trimethacrylate, pentaerythritol triacrylate, and pentaerythritol trimethacrylate; and diallylamine and triallylamine. One kind of cross-linking monomers may be used, or two or more kinds of cross-linking monomers may be used in combination.

In one aspect, the gel material of the present invention is demanded to have high heat resistance to prevent heat deformation and/or the like. The high heat resistance enables use of the gel material at high temperature, and allows application of steam sterilization (commonly at 121° C.) to the medical devices, which is advantageous.

In cases where the gel material of the present invention contains a repeating unit derived from a cross-linking monomer, the gel material has high heat resistance, which is preferred. The content of repeating units derived from cross-linking monomers is preferably 0.01 to 25% by mass with respect to the dry mass of the gel material. The lower limit of the content is preferably 0.1% by mass, more preferably 0.5% by mass, still more preferably 1% by mass, still more preferably 5% by mass. The upper limit of the content is preferably 25% by mass, more preferably 20% by mass, still more preferably 15% by mass, still more preferably 10% by mass. Any combination of the lower limit and upper limit may be employed.

For the gel material of the present invention to be heat-moldable, the gel material preferably does not contain a repeating unit derived from a cross-linking monomer.

The gel material of the present invention is composed mainly of (1) a copolymer comprising a repeating unit derived from the anionic monomer (A) and a repeating unit derived from the cationic monomer (B); or (2) a mixture of a polymer comprising a repeating unit derived from the anionic monomer (A) and a polymer comprising a repeating unit derived from the cationic monomer (B). The gel material preferably comprises the copolymer of (1). The copolymerization herein may be any of random copolymerization, block copolymerization, and branching copolymerization. Each polymer may further comprise a repeating unit derived from the monomer (C). The term "composed mainly of" herein means that the ratio of the polymer in the whole polymer constituting the gel material is more than 50% by mass. The ratio is preferably not less than 70% by mass, more preferably not less than 90% by mass, still more preferably not less than 95% by mass, still more preferably not less than 99% by mass, most preferably 100% by mass. The gel material of the present invention may contain another polymer as long as the effect of the present invention is not inhibited. Examples of the other polymer include amide-based polymers such as polyvinyl pyrrolidone, polyacrylamide, poly(N,N-dimethylacrylamide), and poly(N-methyl-N-vinylacetamide); styrene-based polymers such as polystyrene and polyvinylnaphthalene; (meth)acrylate-based polymers such as polyhydroxyethyl (meth)acrylate, polymethoxyethyl (meth)acrylate, polymethyl (meth)acrylate, polyethyl (meth)acrylate, polyphenyl (meth)acrylate, and polybenzyl (meth)acrylate; polyamino acids such as polyglutamic acid, and polypeptides; polysaccharides such as pullulan, hyaluronic acid, alginic acid, and cellulose, and derivatives thereof; polyesters such as polylactic acid and polyglycolic acid; polyurethanes; and polyethers such as polyethylene oxide. The ratio of the other polymer is one at which the effect of the present invention is not inhibited, and is usually less than 50% by mass, preferably not more than 30% by mass, more preferably not more than 10% by mass, still more preferably not more than 5% by mass, still more preferably not more than 1% by mass, most preferably 0% by mass (which means that the other polymer is not contained).

The gel material of the present invention can be obtained by polymerization of a monomer composition.

The monomer composition may contain a solvent. The solvent is preferably water and/or an organic solvent, more preferably water, a hydrophilic organic solvent, or a mixture of water and a hydrophilic organic solvent, most preferably water. The hydrophilic organic solvent means an organic solvent soluble in water at 20° C. to a concentration of not less than 1% by mass. One kind of solvent may be used, or two or more kinds of solvents may be used in combination.

Preferred examples of the hydrophilic organic solvent include $C_1$-$C_4$ monohydric aliphatic alcohols such as methyl alcohol, ethyl alcohol, and isopropyl alcohol; aliphatic polyhydric alcohols such as ethylene glycol and propylene glycol; ketones such as acetone and methyl ethyl ketone; ethers such as diethyl ether, tetrahydrofuran, dioxane, and diglyme; amides such as N,N-dimethylformamide, N,N-dimethylacetamide, N-methyl-2-pyrrolidone, and 1,3-dimethyl-2-imidazolidinone; sulfur-containing organic solvents such as dimethyl sulfoxide and sulfolane; and acetic acid esters such as methyl acetate and ethyl acetate. These hydrophilic organic solvents may be used individually, or two or more of these may be used in combination. Among these hydrophilic organic solvents, from the viewpoint of obtaining an aqueous gel having both excellent flexibility and high mechanical strength, $C_1$-$C_4$ monohydric aliphatic alcohols and dimethylsulfoxide are preferred. Methyl alcohol, ethyl alcohol, isopropyl alcohol, and dimethyl sulfoxide are more preferred. Isopropyl alcohol and dimethyl sulfoxide are still more preferred.

Regarding the concentration of the monomer composition of the gel material, the lower limit of the total molar concentration of monomer components in the monomer composition (Cm; unit, mol/L) is preferably 0.4, more preferably 1.0, still more preferably 1.5, still more preferably 2.0. The monomer composition may be solvent-free. In cases where the composition contains a solvent, the upper limit of Cm is preferably 5, more preferably 4, still more preferably 3, still more preferably 2.5. Any combination of the lower limit and upper limit may be employed.

Hereinafter, "mol/L" may be expressed as "M".

The monomer composition may contain a chain transfer agent for controlling the molecular weight. Preferred examples of the chain transfer agent include mercaptan-containing compounds such as 2-(dodecylthiocarbonothioylthio)-2-methylpropionic acid, 2-(dodecylthiocarbonothioylthio)propionic acid, methyl 2-(dodecylthiocarbonothioylthio)-2-methylpropionate, 2-(dodecylthiocarbonothioylthio)-2-methylpropionic acid 3-azide-1-propanol ester, 2-(dodecylthiocarbonothioylthio)-2-methylpropionic acid pentafluorophenyl ester, lauryl mercaptan, dodecyl mercaptan, and thioglycerol; and inorganic salts such as sodium hypophosphite and sodium hydrogen sulfite. These chain transfer agents may be used individually, or two or more of these may be used in combination. The amount of the chain transfer agent is usually preferably 0.01 to 10 parts by mass with respect to 100 parts by mass of the total mass of monomer components in the monomer composition.

The monomer composition preferably contains a polymerization initiator. Examples of the polymerization initiator include thermal initiators and photoinitiators.

Preferred examples of the thermal initiators include azo-based polymerization initiators such as azoisobutyronitrile, methyl azoisobutyrate, and azobisdimethylvaleronitrile; and peroxide-based polymerization initiators such as benzoyl peroxide, potassium persulfate, and ammonium persulfate. These polymerization initiators may be used individually, or two or more of these may be used in combination.

In cases where a thermal initiator is used as the polymerization initiator, the amount of the thermal initiator is usually preferably about 0.01 to 20 parts by mass with respect to the 100 parts by mass of the total mass of monomer components in the monomer composition.

Preferred examples of the photoinitiator include 2-oxoglutaric acid, 1-hydroxycyclohexyl phenyl ketone, 2-hydroxy-2-methyl-1-phenylpropan-1-one, 2-methyl [4-(methylthio)phenyl]-2-morpholinopropan-1-one, 2,2-dimethoxy-1,2-diphenylethan-1-one, benzophenone, 1-[4-(2-hydroxyethoxy)phenyl]-2-hydroxy-2-methyl 1-propan-1-one, 2-benzyl-2-dimethylamino-1-(4-morpholinophenyl) butan-1-one, and bis(2,6-dimethoxybenzoyl)-2,4,4- trimethylpentylphosphine oxide. These polymerization initiators may be used individually, or two or more of these may be used in combination.

In cases where a photoinitiator is used as the polymerization initiator, the amount of the photoinitiator is usually preferably about 0.01 to 20 parts by mass with respect to 100 parts by mass of the total mass of monomer components in the monomer composition.

The polymerization reaction temperature of the monomer composition is about 50 to 120° C. The polymerization reaction time of the monomer components is usually about 3 to 20 hours, although it may vary depending on the polymerization reaction temperature and the like.

The polymerization may be multistage polymerization. For example, in the first stage, a monomer composition containing the monomer (A) but not containing the monomer (B) is polymerized to obtain a polymer. In the second stage, a monomer composition containing the monomer (B) but not containing the monomer (A) is mixed with the polymer obtained in the first stage, and the resulting mixture is polymerized to obtain the gel material of the present invention. In the second stage, the polymer may be impregnated with the monomer composition. The monomer (A) and the monomer (B) may be interchanged to change their order.

The following is another example. A monomer composition containing the monomer (A) but not containing the monomer (B) is polymerized to obtain a polymer (a). Separately, a monomer composition containing the monomer (B) but not containing the monomer (A) is polymerized to obtain a polymer (b). Thereafter, the polymer (a) and the polymer (b) are mixed together to obtain the gel material of the present invention.

By placing the monomer composition to a mold having a desired internal shape, and then performing polymerization, a gel material having the shape corresponding to the internal shape of the mold can be obtained. In cases where the monomer composition is flown on a base material, a film-shaped or sheet-shaped gel material having a thickness of, for example, about 50 m to 5 mm can be obtained. In another preferred method, the gel material may be molded into a block-like shape, rod-like shape, or plate-like shape, and may then be subjected to a slicing process, cutting process, turning process, or the like to achieve a desired shape.

The gel material obtained is preferably washed with a solvent (washing solvent) to remove unnecessary components that can be eluted, such as residual monomers and oligomers, and the polymerization solvent. The washing solvent is preferably water, a hydrophilic organic solvent, or a mixture of water and a hydrophilic organic solvent. Preferred examples of the hydrophilic organic solvent used as the washing solvent include those mentioned above. The washing solvent is preferably water, alcohol, or a mixture of water and alcohol. The washing solvent is more preferably water, or a mixture of isopropyl alcohol and water.

The washing of the gel material is commonly carried out by immersing the gel material in the washing solvent, which washing solvent is allowed to flow when necessary.

The washing temperature is preferably within the range of room temperature to 120° C., and the washing time is preferably within the range of 1 minute to 1 month.

The monomer composition may also contain appropriate amounts of additives such as antimicrobial agents, antiseptics, coloring agents, ultraviolet absorbers, perfumes, plasticizers, and antioxidants, as long as the object of the gel material of the present invention is not inhibited.

When necessary, the gel material of the present invention may be provided with a reinforcing material such as a fiber, woven fabric, non-woven fabric, resin sheet, or resin film.

The gel material of the present invention is especially suitable for medical devices. It is suitable for ophthalmic devices such as artificial cornea, ophthalmic lenses, shunts, punctal plugs, and lacrimal catheters. In particular, the gel material is suitable for ophthalmic lenses such as spectacle lenses, corneoscleral lenses, contact lenses, intraocular lenses, and corneal implants, especially suitable for corneoscleral lenses, hard contact lenses, and hybrid contact lenses. A hybrid contact lens herein means a contact lens composed of a combination of a hard material and a soft material. In a representative configuration, the hybrid contact lens is composed of a hard material in the center and a soft material in the periphery thereof. In another representative configuration of the hybrid contact lens, the lens has a multilayer structure comprising: a layer to be in contact with an eyeball, which layer is composed of a soft material; and in addition, a layer composed of a hard material. Since the gel material of the present invention contains water, it has water permeability, and allows tear exchange in the thickness direction. Therefore, the gel material is especially suitable for corneoscleral lenses, which tend not to allow tear exchange because of their limited movement after wearing in the eyes, and for hybrid contact lenses.

EXAMPLES

The present invention is described below more concretely by way of Examples and Comparative Examples.
[Preparation of Sheet]
A gel material sheet was prepared by the following method.

A gel material was obtained by single-stage random copolymerization of sodium p-styrenesulfonate (NaSS), which is an anionic monomer, and (vinylbenzyl)trimethylammonium chloride (VBTA), which is a cationic monomer. Predetermined amounts of NaSS, VBTA, and an ultraviolet polymerization initiator 2-oxoglutaric acid (0.2 mol % with respect to the total number of moles of monomers) were uniformly dissolved in a predetermined amount of water, to prepare a monomer composition. A mold was prepared with two 10-cm square glass plates each having a thickness of 3 mm, and a silicone rubber as a sealer separating the glass plates. By adjusting the thickness of the silicone rubber in accordance with the purpose, the thickness of the sheet obtained was adjusted. The monomer composition was filled into the mold. Polymerization was carried out by irradiation of an ultraviolet ray having an illuminance of 4 mW/cm$^2$ and a wavelength of 365 nm for 10 hours using an ultraviolet irradiator [manufactured by UVP; Product No. 95-0042-12]. The sheet obtained was immersed in a large excess amount of pure water, and left to stand for 2 weeks at room temperature. By this, the water content in the gel material (PNV) was equilibrated, and residual substances after the polymerization that can be eluted were washed out.

Hereinafter, the following abbreviations may be used.
Cm: Total concentration of monomers (M) in the monomer composition.
f: Number of moles of NaSS in the monomer composition/total number of moles of monomers in the monomer composition Hereinafter, a PNV sample prepared under each condition may be represented by an abbreviation such as PNV-Cm-f.

[Measurement of Volume Swelling Ratio]

A gel material sheet was prepared using a silicone rubber having a thickness of 2 mm. The central portion of the gel material sheet immediately after the polymerization was cut out (about 5 cm×about 5 cm). The length of one specific side of the sheet was precisely measured using a vernier caliper. The sheet was immersed in a large excess amount of pure water, and left to stand at room temperature for 2 weeks. By this, the water content in the gel material was equilibrated, and residual substances after the polymerization that can be eluted were washed out. The length of the one specific side of the sheet obtained was precisely measured using a vernier caliper. The ratio between (the length of the side of the sheet after the equilibration) and (the length of the side of the gel immediately after the polymerization) was raised to the power of 3 to determine the volume swelling ratio.

[Measurement of Water Content]

The mass (M1) of gel material sheets (about 2.5 cm×about 2.5 cm, two sheets), prepared using a silicone rubber having a thickness of 2 mm, in the water-containing state was measured. Thereafter, the sheets were brought into the dry state, and their mass (M2) was measured. The measurement was carried out using a precision balance.

[Tensile Test]

A gel material sheet prepared using a silicone rubber having a thickness of 2 mm was punched into the No. 7 dumbbell shape defined by JIS K6251 (whose measurement portion has a length of 12 mm and a width of 2 mm), and fixed to a universal tester TENSILON RTC-1310A manufactured by ORIENTEC using a special chuck. A tensile test was then carried out at a rate of 100 mm/min. The tensile stress at break was determined according to the formula "the force at tensile break/the original cross-sectional area", and the tensile elongation at break was determined according to the formula "the length at tensile break/the original length". The angle of the linear portion in the early part of the tensile stress-strain curve was defined as the tensile elastic modulus. When the sample is a contact lens, a piece cut out into a strip shape having a width of 3 mm may be used to perform the same tensile test.

[Measurement of Static Contact Angle of Water]

Measurement was carried out using a DropMaster 300 Contact Angle Meter (Kyowa Interface Science Co., Ltd.). Using a hydrophobized syringe, 2.0-μL water droplets were carefully placed on a surface of a gel material sheet (in the water-containing state). The water droplets were placed at not less than five different positions on each sample, and their contact angles were measured, followed by calculating the average.

[Differential Scanning Calorimetry Analysis (DSC)]

DSC analysis was carried out using EXSTAR X-DSC700 (EXSTAR, Japan). First, a sample (5.0 to 8.0 mg) cut out from a gel material sheet (in the water-containing state) was cooled to −80° C. at a cooling rate of 50° C./min. The sample was kept at −80° C. for 10 minutes, and then heated to 30° C. at a heating rate of 5° C./min.

[Wide-Angle X-Ray Diffraction (WAXD)]

The WAXD pattern was measured with an X-ray having a wavelength of 0.124 nm using beamline BL16B1 [Shanghai Synchrotron Radiation Facility (SSRF)]. The measurement was carried out using an X-ray diffractometer RU-200 (manufactured by Rigaku Corporation) under the following conditions:

X-ray source: CuKα ray (Ni filter)
Temperature: 25° C.
Output: 40 kV-200 mA
Sample-detector distance: 137 mm
Measurement range: 2θ=7° to 40°
Scanning rate: 2°/min
Sample (in the water-containing state): 1.35-mm thickness
Sample (in the dry state): powder

[Visible Light Transmittance]

Transparency of a gel material sheet (in the water-containing state, 1.35-mm thickness) was evaluated. The measurement was carried out using a UV-1800 ultraviolet-visible light spectrophotometer (manufactured by Shimadzu Corporation) at 24° C. The measurement was carried out within a wavelength range of 800 nm to 400 nm.

[Evaluation of Dynamic Viscoelasticity]

Measurement was carried out using an ARES rheometer (manufactured by TA Instruments). A gel material sheet (in the water-containing state, about 1.3-mm thickness) was cut into a disk having a diameter of 15 mm, to provide a measurement sample. The sample was adhered to a plate using a cyanoacrylate-based adhesive "Aron Alpha" (manufactured by Konishi Co., Ltd.), and then surrounded by water to keep the hydrated state. A temperature sweep test was carried out under the following conditions: frequency range, 0.1 Hz to 100 Hz; shearing strain, 10%. A frequency sweep test was carried out under the following conditions: frequency range, 0° C. to 90° C.; temperature range: 0° C. to 88° C.

Examples 1 to 7, and Comparative Examples 1 to 14

According to the method described in [Preparation of Sheet], gel material sheets were prepared with the Cm's and f's listed in Table 1.

TABLE 1

|  | Cm | f |
|---|---|---|
| Comparative Example 1 | 2.5 | 0.10 |
| Comparative Example 2 | 2.5 | 0.20 |
| Comparative Example 3 | 2.5 | 0.30 |
| Comparative Example 4 | 2.5 | 0.40 |
| Comparative Example 5 | 2.5 | 0.45 |
| Comparative Example 6 | 2.5 | 0.48 |
| Example 1 | 2.5 | 0.50 |
| Example 2 | 2.5 | 0.52 |
| Example 3 | 2.5 | 0.54 |
| Example 4 | 2.5 | 0.56 |
| Comparative Example 7 | 2.5 | 0.58 |
| Comparative Example 8 | 2.5 | 0.60 |
| Comparative Example 9 | 2.5 | 0.70 |
| Comparative Example 10 | 0.05 | 0.52 |
| Comparative Example 11 | 0.10 | 0.52 |
| Comparative Example 12 | 0.30 | 0.52 |
| Comparative Example 13 | 0.50 | 0.52 |
| Comparative Example 14 | 1.00 | 0.52 |
| Example 5 | 1.50 | 0.52 |
| Example 6 | 2.00 | 0.52 |
| Example 7 | 2.50 | 0.52 |

[Evaluation of Volume Swelling Ratio and Water Content of PNV-2.5-f]

Figure 1:
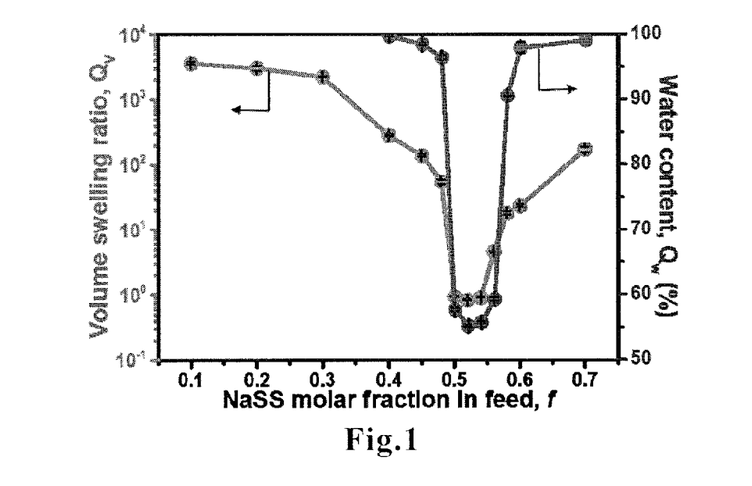
FIG. 1 is a diagram showing the results of measurement of the volume swelling ratio (Qv) and the water content (Qw) in the Examples and Comparative Examples described below.

For Examples 1 to 4 and Comparative Examples 1 to 9, the volume swelling ratio (Qv) and the water content (Qw) were evaluated. The results are shown in FIG. 1.

[Evaluation of Tensile Stress at Break and Tensile Elastic Modulus of PNV-2.5-f]

Figure 2:
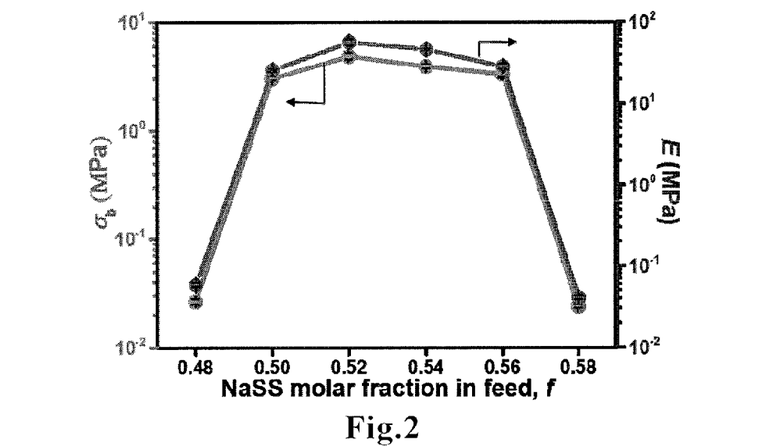
FIG. 2 is a diagram showing the results of measurement of the tensile stress at break (Gb) and the tensile elastic modulus (E) in the Examples and Comparative Examples described below.

For Examples 1 to 4 and Comparative Examples 1 to 9, the tensile stress at break (σb) and the tensile elastic modulus (E) were evaluated. The results are shown in FIG. 2.

[Evaluation of Volume Swelling Ratio and Water Content of PNV-Cm-0.52]

Figure 3:
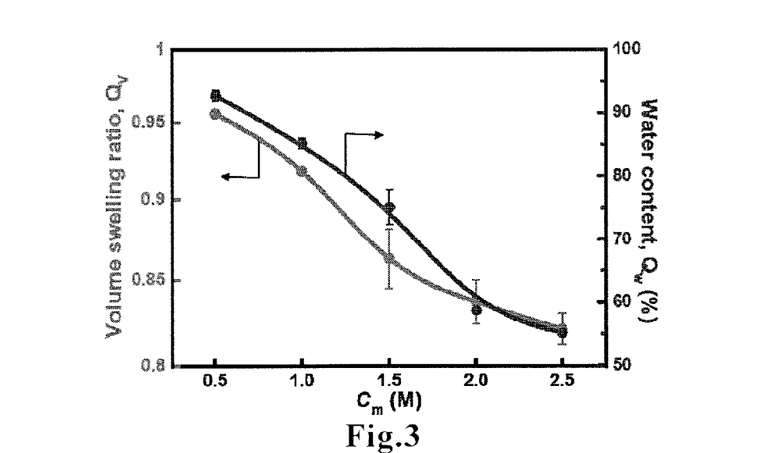
FIG. 3 is a diagram showing the results of measurement of the volume swelling ratio (Qv) and the water content (Qw) in the Examples and Comparative Examples described below.

For Examples 5 to 7 and Comparative Examples 10 to 14, the volume swelling ratio (Qv) and the water content (Qw) were evaluated. The results are shown in FIG. 3. In Comparative Examples 10 to 12 (Cm, 0.05 to 0.3), gel materials were not formed even after the polymerization since Cm was too low.

[Tensile Test of PNV-Cm-0.52]

For Examples 5 to 7 and Comparative Examples 13 and 14, a tensile test was carried out.

Figure 4:
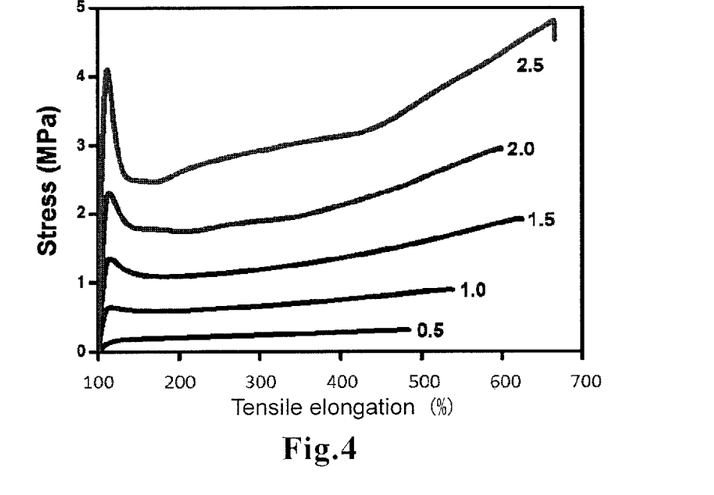
FIG. 4 is a diagram showing the relationship between the tensile elongation and the stress measured in the Examples and Comparative Examples described below.

The relationship between the tensile elongation and the stress was as shown in FIG. 4. The numbers 0.5 to 2.5 shown beside the curves in the figure represent Cm (M).

Figure 5:
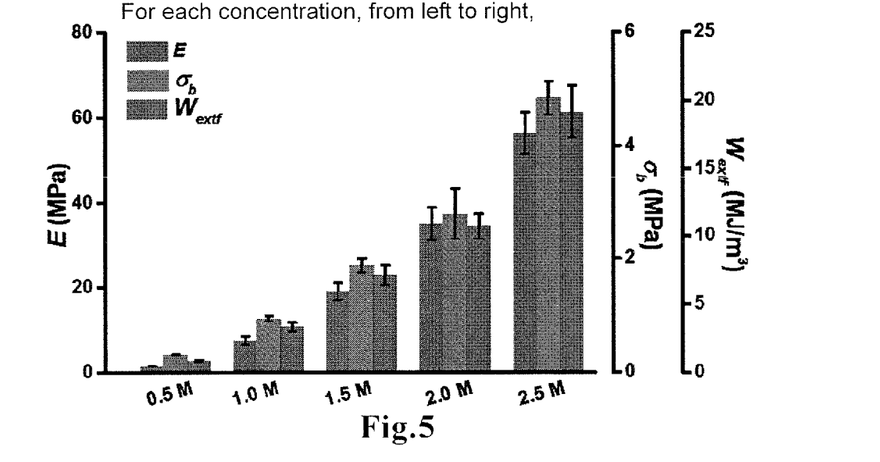
FIG. 5 is a diagram showing the measurement results in the tensile test in the Examples and Comparative Examples described below.

The results of the tensile test are shown in FIG. 5. In FIG. 5, the abscissa represents Cm. In the graph, combinations of three vertical bars are drawn. In each combination, the bars represent, from left to right, the tensile elongation at break (E), the tensile stress at break (b), and the tensile work at break (Wextf).

The tensile work at break was calculated by integrating the stress values on the stress-strain curve from zero strain to the break. Thus, the tensile work at break corresponds to the area surrounded by the stress-strain curve and the abscissa.

[Evaluation of Heat Moldability of PNV-2.5-0.52]

Heat moldability of PNV-2.5-0.52 was investigated by the following procedure.

Figure 6:
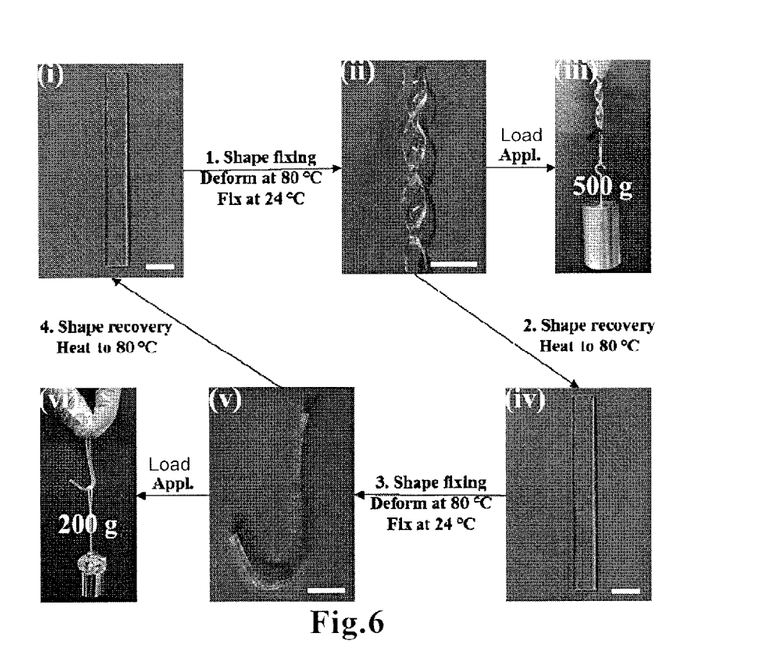
FIG. 6 is a diagram illustrating the method of evaluation of the heat moldability, which was carried out in the Examples described below.

The sheet of Example 2, prepared using a silicone rubber having a thickness of 2 mm, was cut into a strip having a width of 1 cm and a length of 10 cm [FIG. 6(i)]. The strip was immersed in water at 80° C. for 1 minute, and then twisted, followed by immersion in water at room temperature [FIG. 6(ii)]. The strip was found to be heat-moldable since its shape was fixed in the twisted state. With the twisted strip, a 500-g weight could be suspended [FIG. 6(iii)]. The original shape was recovered by immersing the twisted strip in water at 80° C. for 1 minute. Thereafter, the strip was immersed in water at room temperature [FIG. 6(iv)]. The resulting strip was immersed in water at 80° C. for 1 minute, and then bent into a hook shape. The strip was then immersed in water at room temperature [FIG. 6(v)]. This resulted in fixation of the hook shape of the strip. With the hook obtained, a 200-g weight could be suspended [FIG. 6(vi)].

[Evaluation of Properties of PNV-2.5-0.52]

PNV-2.5-0.52 (Example 2) was evaluated.

The static contact angle of water on the surface of the sheet (in the water-containing state) was 55°, indicating the surface wettability.

The water content was 55.2%. According to evaluation by the DSC analysis, the water in the gel material was found to be composed of 28% free water and 72% unfreezable water or intermediate water.

As a result of the wide-angle X-ray diffraction measurement, crystallinity was found neither in the water-containing state nor in the dry state.

Figure 7:
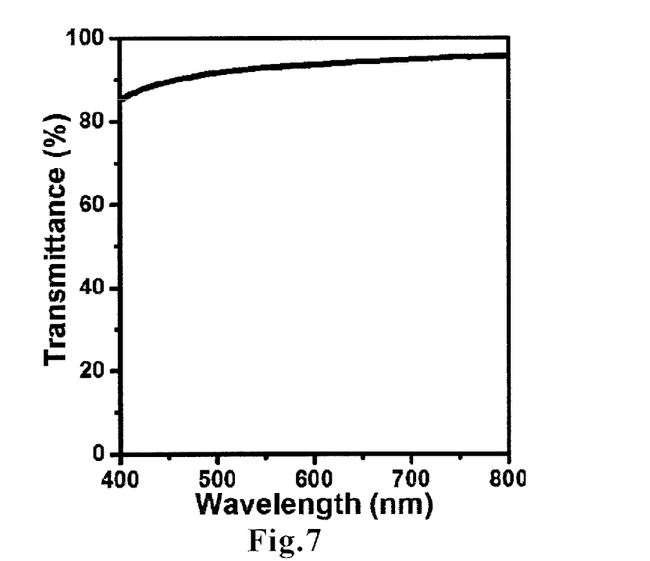
FIG. 7 is a diagram showing the results of measurement of the visible absorption spectrum in the Examples and Comparative Examples described below.

As a result of measurement of the visible light transmittance, the visible light transmittance of the gel material sheet was found to be not less than 82% throughout the region, indicating that the gel material is colorless and transparent (FIG. 7).

[Evaluation of Thermal Stability of PNV-2.5-0.52]

Thermal stability of PNV-2.5-0.52 (Example 2) was evaluated.

Figure 8:
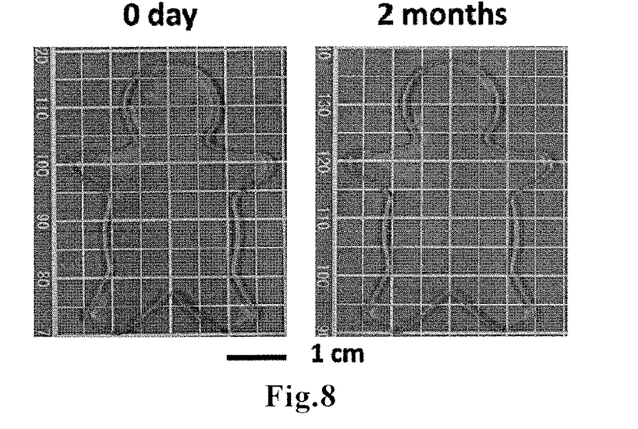
FIG. 8 is a diagram showing comparison of the size of the sheet of Example 2 described below, wherein the sheet was cut into a human shape, and stored in water at 60° C. for 2 months, followed by changing the temperature to room temperature before the comparison.

The sheet of Example 2 was cut into a human shape, and stored in water at 60° C. for 2 months. After changing the temperature to room temperature, the size was compared with that before the storage. As a result, no change was found (FIG. 8).

Figure 9:
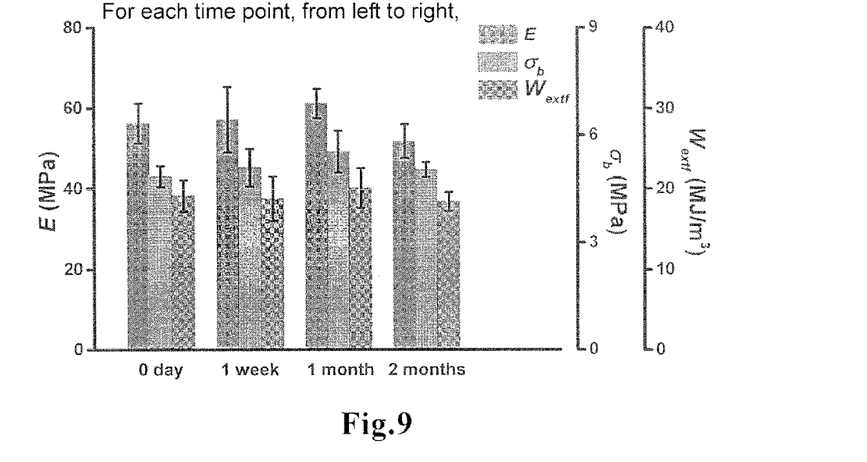
FIG. 9 is a diagram showing the results of a tensile test, wherein the sheet of Example 2 was stored in water at 60° C. for 1 week, 1 month, or 2 months, and then the temperature was changed to room temperature before the test.

The sheet of Example 2 was stored in water at 60° C. for 1 week, 1 month, or 2 months. The temperature was changed to room temperature, and a tensile test was carried out (FIG. 9). In FIG. 9, the abscissa represents the storage period. In the graph, combinations of three vertical bars are drawn. In each combination, the bars represent, from left to right, the tensile elongation at break (E), the tensile stress at break ((ab), and the tensile work at break (Wextf). Since none of the physical property values showed a large change from the value before the storage, the sheet was found to have excellent thermal stability.

[Measurement of Dynamic Viscoelasticity of PNV-Cm-0.52]

Figure 10:
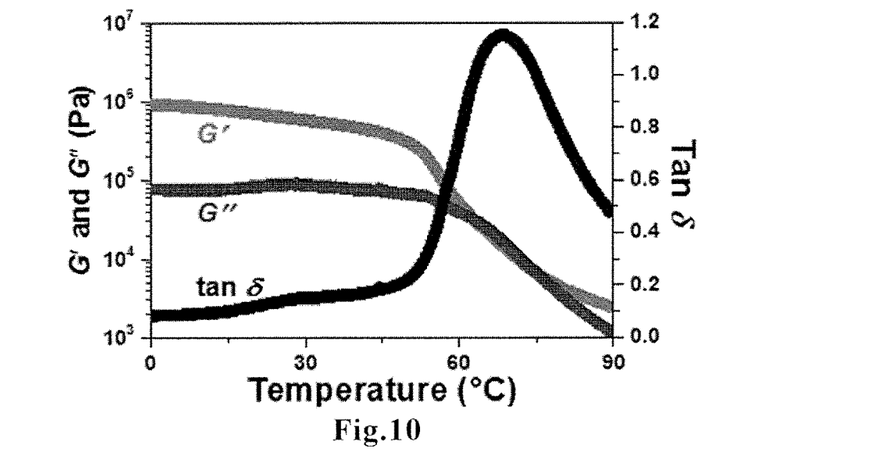
FIG. 10 is a diagram showing the result of measurement of the dynamic viscoelasticity of the sheet of the Comparative Example 13 described below.
Figure 11:
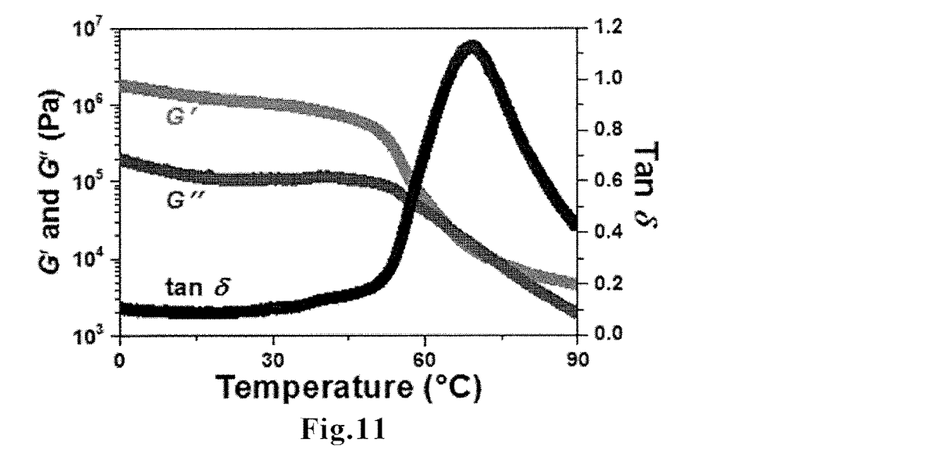
FIG. 11 is a diagram showing the result of measurement of the dynamic viscoelasticity of the sheet of the Comparative Example 14 described below.
Figure 12:
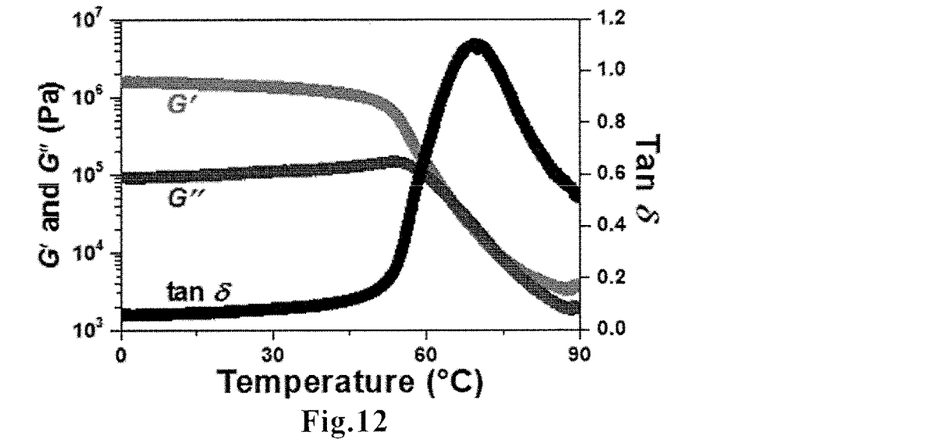
FIG. 12 is a diagram showing the result of measurement of the dynamic viscoelasticity of the sheet of the Example 5 described below.
Figure 13:
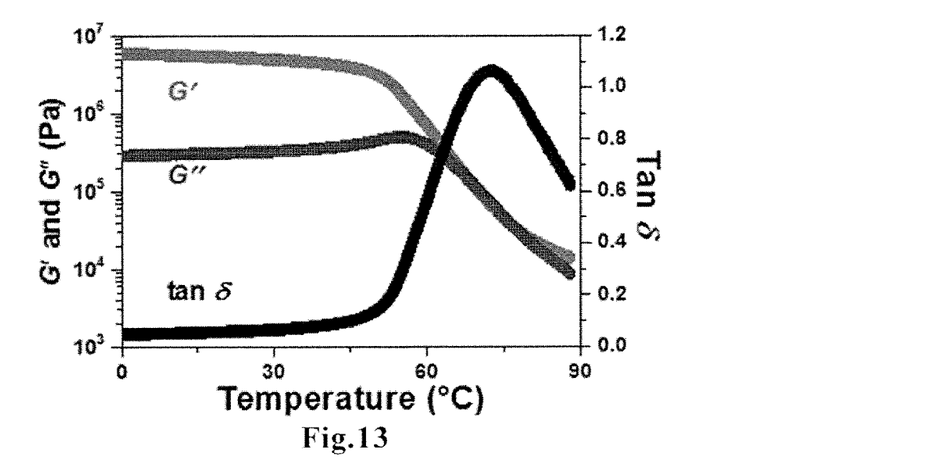
FIG. 13 is a diagram showing the result of measurement of the dynamic viscoelasticity of the sheet of the Example 6 described below.
Figure 14:
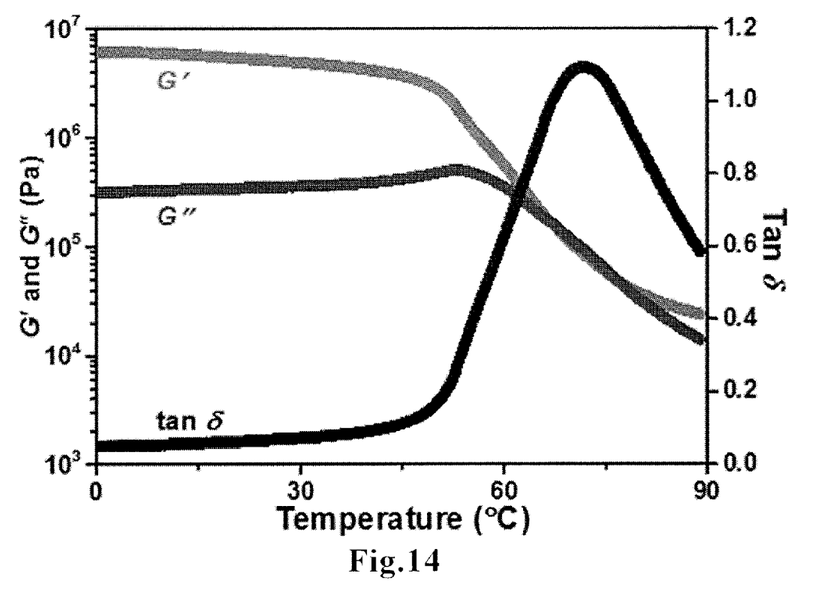
FIG. 14 is a diagram showing the result of measurement of the dynamic viscoelasticity of the sheet of the Example 7 described below.

The sheets obtained in Comparative Example 13, Comparative Example 14, and Examples 5 to 7 in the water-containing state were subjected to measurement of the dynamic viscoelasticity. The results are shown in FIG. 10 (Cm=0.5), FIG. 11 (Cm=1.0), FIG. 12 (Cm=1.5), FIG. 13 (Cm=2.0), and FIG. 14 (Cm=2.5). In FIGS. 10 to 14, G' represents the storage modulus; G" represents the loss elastic modulus; and Tan δ represents the loss tangent.

The invention claimed is:

1. A gel material comprising repeating units derived from the following monomers (A) and (B):
   (A) an anionic monomer containing a polymerizable carbon-carbon multiple bond and an aromatic ring; and
   (B) a cationic monomer containing a polymerizable carbon-carbon multiple bond and an aromatic ring;
   the gel material having
   a water content of 20% by mass to 95% by mass,
   a tensile elastic modulus of 9 MPa to 1000 MPa, and
   a tensile elongation at break of 200% to 5000%,
   wherein the lower limit of the total molar concentration of monomer components in the monomer composition (Cm; unit, mol/L) is 2.0 and
   wherein the ratio (mol/mol) between the repeating units derived from the monomer (A) and the repeating units derived from the monomer (B) is within the range of 35/65 to 75/25.

2. The gel material according to claim 1, which is heat-moldable at a temperature within the range of 60° C. to 250° C.

3. The gel material according to claim 1, comprising a copolymer containing repeating units derived from the monomers (A) and (B).

4. The gel material according to claim 1, wherein the (A) is an anionic monomer represented by the following Formula (1):

wherein $X^1$ represents a group selected from the group consisting of (meth)acryloyl and vinyl;

$Z^1$ represents a group selected from the group consisting of sulfo and carboxy, or a salt thereof;

$L^1$ and $L^2$ each independently represent a direct bond, or $C_1$-$C_{10}$ alkylene;

$Y^1$ represents a direct bond, or a group selected from the group consisting of O, S, and N—$R^2$;

$Y^2$ represents a direct bond, or a group selected from the group consisting of O, S, N—$R^3$, OCO, and N—$R^4$CO;

$R^1$ represents a group selected from the group consisting of $C_1$-$C_{10}$ alkyl, phenyl, halogeno, and hydroxy;

$R^2$ to $R^4$ each independently represent hydrogen, or a group selected from the group consisting of $C_1$-$C_{10}$ alkyl and phenyl; and m represents an integer of 0 to 4.

5. The gel material according to claim 4, wherein
the $L^1$ and $L^2$ are each independently a direct bond or $C_1$-$C_5$ alkylene;
the $Y^1$ and $Y^2$ are direct bonds; and
the $R^1$ is $C_1$-$C_5$ alkyl.

6. The gel material according to claim 1, wherein the (B) is a cationic monomer represented by the following Formula (2):

wherein
$X^3$ represents a group selected from the group consisting of (meth)acryloyl and vinyl;
$Z^3$ represents amino or a salt thereof;
$L^3$ and $L^4$ each independently represent a direct bond, or $C_1$-$C_{10}$ alkylene;
$Y^3$ represents a direct bond, or a group selected from the group consisting of O, S, and N—$R^6$;
$Y^4$ represents a direct bond, or a group selected from the group consisting of O, S, N—$R^7$, OCO, and N—$R^8$CO;
$R^5$ represents a group selected from the group consisting of $C_1$-$C_{10}$ alkyl, phenyl, halogeno, and hydroxy;
$R^6$ to $R^8$ each independently represent hydrogen, or a group selected from the group consisting of $C_1$-$C_{10}$ alkyl and phenyl; and
n represents an integer of 0 to 4.

7. The gel material according to claim 6, wherein
the $Z^3$ is a quaternary ammonium salt;
the $L^3$ and $L^4$ are each independently a direct bond or $C_1$-$C_5$ alkylene;
the $Y^3$ and $Y^4$ are direct bonds; and
the $R^5$ is $C_1$-$C_5$ alkyl.

8. The gel material according to claim 1, wherein the (A) is an anionic monomer selected from the group consisting of benzyl (meth)acrylate-based anionic monomers, benzyl (meth)acrylamide-based anionic monomers, phenyl (meth)acrylate-based anionic monomers, phenyl (meth)acrylamide-based anionic monomers, and styrene-based anionic monomers.

9. The gel material according to claim 1, wherein the (B) is a cationic monomer selected from the group consisting of benzyl (meth)acrylate-based cationic monomers, benzyl (meth)acrylamide-based cationic monomers, phenyl (meth)acrylate-based cationic monomers, phenyl (meth)acrylamide-based cationic monomers, and styrene-based cationic monomers.

10. The gel material according to claim 1, wherein the (A) is styrenesulfonic acid or a salt thereof.

11. The gel material according to claim 1, wherein the (B) is dialkylaminoalkyl styrene or a salt thereof.

12. The gel material according to claim 11, wherein the (B) is (vinylbenzyl)trimethylammonium chloride.

13. The gel material according to claim 1, which is optically transparent.

14. A medical gel material comprising the gel material according to claim 1.

15. An ophthalmic gel material comprising the medical gel material according to claim 14.

16. An ophthalmic lens gel material comprising the ophthalmic gel material according to claim 15.

17. A medical device comprising the medical gel material according to claim 14.

18. The medical device according to claim 17, which is an ophthalmic lens.

* * * * *